United States Patent [19]

Chadney et al.

[11] Patent Number: 5,554,539
[45] Date of Patent: Sep. 10, 1996

[54] DETERMINATION OF AN ANALYTE

[75] Inventors: Donovan C. Chadney, Chinnor; Kevin P. J. Doyle, Tring, both of England

[73] Assignee: Johnson & Johnson Clinical Diagnostics, Inc., Rochester, N.Y.

[21] Appl. No.: 360,481

[22] Filed: Dec. 21, 1994

[30] Foreign Application Priority Data

Dec. 22, 1993 [GB] United Kingdom ............... 93026197
Jun. 17, 1994 [GB] United Kingdom ............... 94012141

[51] Int. Cl.$^6$ .................................................. G01N 31/00
[52] U.S. Cl. .................... 436/8; 364/571.01; 364/571.05
[58] Field of Search .................................. 436/8.63, 824; 73/1 R; 364/571.01, 571.04, 571.05

[56] References Cited

U.S. PATENT DOCUMENTS

| | | | |
|---|---|---|---|
| 4,832,488 | 5/1989 | Hirai et al. | 356/243 |
| 5,122,969 | 6/1992 | Seshimoto et al. | 364/497 |
| 5,255,204 | 10/1993 | Saito et al. | 364/497 |
| 5,257,212 | 10/1993 | Kildal-Brandt et al. | 364/582 |
| 5,332,479 | 7/1994 | Veroyama et al. | 204/153.12 |
| 5,348,889 | 9/1994 | Terashima et al. | 436/8 |

FOREIGN PATENT DOCUMENTS

| | | |
|---|---|---|
| 0247439 | 12/1987 | European Pat. Off. . |
| 0266216 | 5/1988 | European Pat. Off. . |
| 0305563 | 3/1989 | European Pat. Off. . |
| 0383322 | 8/1990 | European Pat. Off. . |
| 0422646 | 4/1991 | European Pat. Off. . |
| 0567093 | 10/1993 | European Pat. Off. . |

OTHER PUBLICATIONS

DataBase WPI, Week 8828, Derwent Publications, Ltd., GB; AN 88–194333 & JP-A-63 132 166 (Olympus Optical KK), Jun. 1988–abstract.

Patent Abstracts of Japan, vol. 010 No. 127 (P-487), 15 Aug., 1986 & JP-A-61 068539 (Omron Tateisi Electronics Co.) Apr. 1986–abstract.

*Primary Examiner*—James C. Housel
*Assistant Examiner*—Rachel Heather Freed
*Attorney, Agent, or Firm*—Dana M. Schmidt

[57] ABSTRACT

A method and kit are disclosed for recalibrating a factory-prepared relationship between concentration and expected signal $R_{exp}$ produced by an analyzer. The method and kit use two or three calibrators at the field to obtain an actual signal $R_{act}$ for the two calibrators $C_{low}$ and $C_{high}$, for example, and these two actual signals are used to create a ratio of $R_{actlow}/R_{explow}$ and $R_{acthigh}/R_{exphigh}$. The first of these is used to correct the expected signals for concentrations below the lower calibrator concentration, and the second is used to correct expected signals for concentrations above the higher calibrator concentration, producing pseudosignals $PS_{low}$ and $PS_{high}$. A straight-line relationship is applied between the corrected $PS_{low}$ and $PS_{high}$, and that relationship is used for concentrations between $C_{low}$ and $C_{high}$.

4 Claims, 5 Drawing Sheets

DETERMINATION OF AN ANALYTE

FIELD OF THE INVENTION

This invention relates to the determination of the concentration of a specific substance or analyte, suitably in a liquid sample, and to a kit which can be used to make the determination.

BACKGROUND OF THE INVENTION

Immunodiagnostic kits provide means for determining the concentrations of specific substances, usually referred to as analytes, in liquid samples. Generally the liquid samples to be analyzed are biological fluids.

Manufacturers of diagnostic kits frequently supply instruments and software in addition to reagents. Combinations of these are referred to as "diagnostic systems" and are used to generate test results. Generally the user needs to provide only the samples to be assayed and to follow the manufacturer's instructions, although the degree to which physical handling and data processing are automated varies significantly between different systems.

All present systems require the construction of some form of calibration or dose-response curve. Such a curve is assay-specific and comprises a plot of analyte concentration (i.e. dose) against signal (i.e. analytical response). A dose response curve is established by measuring the signals generated from known concentrations of the analyte. These are usually supplied by the kit manufacturer as "calibraters". Generally the dose response curve will be non-linear and its shape can change with different lots of reagents and with the age of the reagents. When constructed the dose response curve is used to translate the signals measured with biological samples into analyte concentrations. Calibration curves are required because reagent aging and transport together with individual instrument responses may affect curve shape and signal level. Calibration is therefore performed in the customer's own laboratory and may be reagent lot-, reagent shipment or instrument-specific. Previously, with most systems it has been necessary for users to batch up samples for future analysis. In batch analysis, the user will usually find it necessary to set up a complete calibration curve every time a group of samples is assayed. To give an idea of the scale of the laboratory effort involved, a full calibration curve for an assay done using the "AMERLITE" (trade mark) system of Kodak Clinical Diagnostics Limited of Amersham, Buckinghamshire, UK requires use of six calibrators in duplicate. It is thus apparent that the larger the batch of samples then the lower the net cost of calibration per test result.

Random access testing is now becoming popular. This allows the user to nominate any test or tests on any sample at any time. There is no need for a user to retain samples until a reasonable batch size has been attained since individual samples can be presented for testing as required.

In order to control the cost of calibration, some form of reduced calibration is required for random access analyzers. In the absence of this, the cost of establishing a full calibration curve every time a sample is presented will be prohibitive. This is the subject of the invention of the present application.

SUMMARY OF THE INVENTION

In accord with one aspect of the invention, there is provided a method of recalibrating in an analyzer, a calibration relationship between concentrations of analyte and analyzer-generated signals corresponding to those concentrations, using a factory-prepared relationship for N number of concentrations, wherein each concentration has an expected signal value $R_{exp}$. The method comprises the steps of:

a) selecting at least two calibrators of low and high concentrations, respectively, ($C_1$ and $C_2$) that are optionally independent of the value of the concentrations of the N number;

b) ascertaining the actual signals $R_{act1}$ and $R_{act2}$ produced by each of the two calibrators in the analyzer;

c) ascertaining which of the N concentrations $(C_i)_{low}$ have a value below the low concentration-selected calibrator of step a) and which concentrations $(C_i)_{high}$ have a value greater than the high concentration-selected calibrator of step a);

d) forming the ratio of $R_{act1}/R_{exp1}$ and $R_{act2}/R_{exp2}$, where $R_{exp1}$ and $R_{exp2}$ are the predicted signals expected for concentration $C_1$ and $C_2$ using the factory-prepared relationship;

e) producing a pseudo-signal for each of the concentrations $(C_i)_{low}$ by multiplying each signal $(R_{exp})_{low}$ for each of the below concentration values by the ratio $R_{act1}/R_{exp1}$ and a pseudosignal for each of the concentrations $(C_i)_{high}$ by multiplying each siganl $(R_{exp})_{high}$ for each of the greater concentration values by the ratio $R_{act2}/R_{exp2}$;

f) for each of the remaining concentrations having values between $C_1$ and $C_2$, producing a pseudosignal $PS_{remainder}$ in accord with the following formula:

$$PS_{remainder}=(R_{act2}-R_{act1})/(R_{exp2}-R_{exp1})\cdot (R_{expremainder}-R_{exp1})+R_{act1};$$

g) ascertaining the relationship for the pseudosignals so obtained in steps e)–f) versus the concentration values for N concentrations; and h) providing a best curve fit for data points between the N values to obtain the recalibrated relationship.

In accord with another aspect of the invention, there is provided a test kit for the determination of an analyte in an assay, the kit comprising the components for performing the assay and calibration information by which signals obtained from at least two calibrators can be used to correct points on a factory-prepared curve for the assay in accordance with the above-noted method.

DESCRIPTION OF THE PREFERRED EMBODIMENTS

Figure 1:
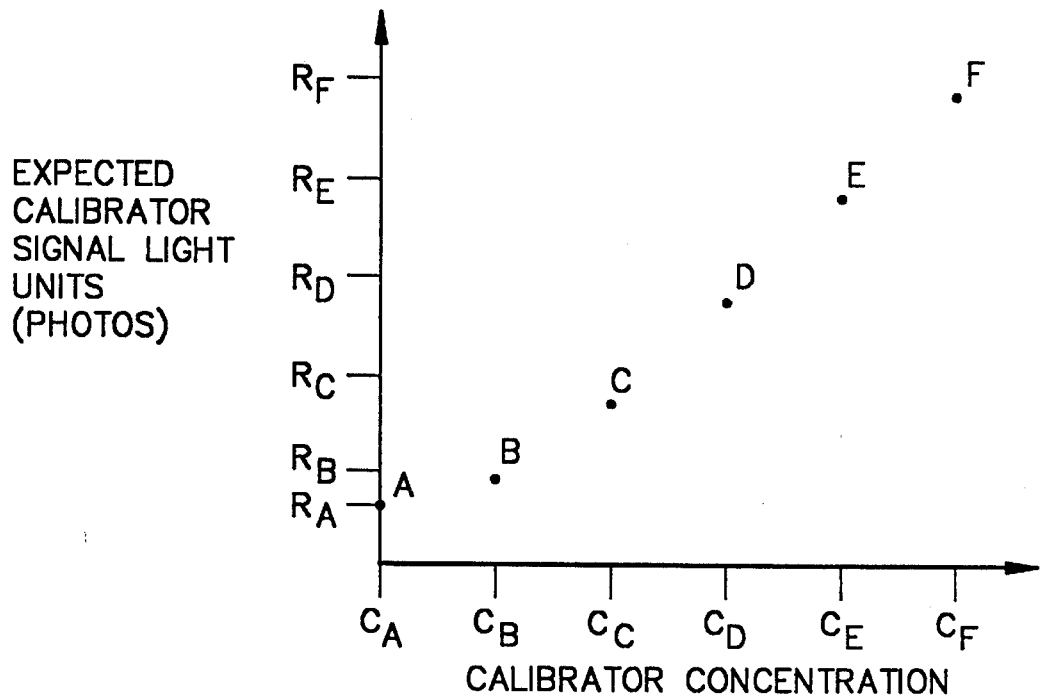
FIGS. 1–5 are plots of calibration data, showing the progression from the factory-prepared relationship, FIG. 1, to the recalibrated relationship, FIG. 5, achieved on the field analyzer.

Suitably the invention is applied to assays for the quantitative determination of analytes and preferably to heterogeneous assays. In particular the invention is useful for assays performed in coated wells, i.e., in vessels (especially plastic vessels) coated with biological material.

The template information may be in any suitable form including a bar code, magnetic card, manual data entry or any other means by which the information provided may be introduced to calibration software previously supplied to a user of the method of the invention. Such bar codes and magnetic cards are conventional. The calibration software interprets the template information and enables a calibration curve to be produced.

In the assay method of the invention a calibrated curve is constructed from a pre-determined curve by dividing the latter into sections, re-scaling each section separately in a linear manner and combining the separately re-scaled sections. This re-calibration method can be described as a piece-wise linear re-scaling method. Generally the pre-determined curve will be produced by the manufacturer of the assay kit to be used whilst the calibrated curve will generally be produced at the point of use.

In the assay method of the invention any suitable number of calibrators can be used. To obtain reduced calibration the number of calibrators used is less than the number that is used as a standard practice in the assay concerned, i.e. if the standard practice is to use n calibrators then to obtain reduced calibration the number of calibrators used is in the range 2 to n−1. However for reduced calibration to be worthwhile there is suitably a substantial reduction in the number of calibrators used as compared with standard practice. In the method of the invention it is preferred therefore that two or possibly three calibrators are used.

Typically the data processing for reduced calibration using the invention includes the following features:

a) preparation of template information in the form of a manufacturer generated calibration curve (MGCC), usually including test criteria for acceptability of the data;

b) recalibration of MGCC data to reduced internal (i.e. run on the instrument) calibration data, deriving pseudo calibrator data from the MGCC data for subsequent curve-fitting;

c) fitting of functional forms to the assay data, MGCC or pseudo calibrators, usually including test criteria for acceptability of both the numerical fit of the curve to the assay data and of the shape characteristics; and d) reporting of the sample concentration returned for the sample signal by interpolation from the fitted curve.

The MGCC data is suitably prepared in the manner described below.

The objective of a MGCC is to provide a set of "representative" assay calibrator signals and concentration data, which can be stored in an assay processing instrument previously supplied to a user of the test kit. To achieve this it is preferred that sufficient assays are performed from any new batch of reagents.

The representative data set is suitably obtained by linear combination of a multiplicity of data sets into a single "pooled" data set. Preferably between 10 and 20 assays are included when building an MGCC data set, this number being suitable to attain sufficient confidence that the "pool" is representative.

Suitable quality control parameters can be applied in order to establish that the shape of a curve has not altered significantly to degrade the performance of the reduced calibration method. The quality of an MGCC data set is preferably checked by one or more of the three methods described below, each method testing quite distinct qualities. The three methods are as follows:

1) checking the % CV (coefficient of variation) spread at each pooled data point, thus checking that the partic004pating data have a variance compatible with that of the underlying population variance;

2) checking that the shape of the assay data is acceptable by checking the signal deltas (defined below) between the pooled calibration data; and 3) checking the intensity of the highest signal.

In this specification the definition of deltas is to be taken to be the differences between adjacent calibrator signal values, normalized by division by the highest signal value. A set of delta limits will therefore bound the allowed shape for an assay curve separately from the light index check. Preferably the % CV is checked against an estimated "population" % CV accumulated continuously by quality control.

Preferably the signal deltas are checked against delta limits laid down by quality control. These limits control the suitability of the data set for clinical assay requirements.

The intensity of the highest signal is preferably checked against limits laid down by quality control for any particular analyte.

Before a set of MGCC data is released, a curve fit to the data is suitably performed and checked for a satisfactory curve fit factor. The curve fit factor is defined as below in item 2.

Fitting of curves to signal and concentration data is carried out at several stages during the usual data processing of the method of the invention. A preferred package of curve fitting routines includes the features set out below.

1) Non-linear least-squares fitting of a modified logistic function, the modification being selected for best representation of the signal data from immunometric assays and competitive assays.

2) Curve fit factor calculation. The curve fit factor is a figure of merit that indicates the worst-case fractional difference between any signal data point and the fitted curve. If the signal data has replicates then the fit factor will be poor either if the spread of replicates is too great or if the curve fit is poor.

3) Interpolation and extrapolation routines which return both signal-from-concentration and concentration-from-signal values.

During routine use of the assay processing instrument, the MGCC data are preferably used to define the shape of the curve. When re-calibrating, at least two calibrators are measured (preferably two). These calibrators need not have the same concentration as the calibrators that were used when the MGCC data was created. The method of re-calibration is based on a piece-wise linear re-scaling method. A preferred method has the steps set out below.

1) A curve is fitted to the MGCC signal and concentration data.

2) Reference calibrator signals are read off the curve at the calibrator concentration values.

3) The MGCC signal data are re-scaled to become pseudo signal data using the piece-wise linear method, scaling the MGCC data such that the scaled reference calibrator signals are made equal to the actual calibrator signals. The MGCC and pseudo data have common concentration values. Thus if the MGCC has, for example, six reference points and there are two calibrators the pseudo data will have six points if two of the MGCC data points correspond to the calibrator concentrations or eight if they do not. If the MGCC has seven reference points and there are two calibrators the pseudo data will have seven or nine points respectively.

4) A curve is fitted to the pseudo signal and actual concentration data to create an instrument generated calibration curve (IGCC).

5) Sample concentration values are read off this curve using the signal values obtained in assays for analytes in the samples.

The quality of the re-calibration may be monitored in one or more of a number of ways. Suitable ways include a) checking the curve fit factor for the IGCC data curve fit; b) checking the deltas for the IGCC signal data; and c) checking the highest IGCC signal data. These checks are for three distinct attributes. The delta checks are for assurance that the DATA SHAPE properly represents an assay for the specific analyte, whereas the curve fit factor checks for a satisfactory numerical fit of the functional curve to that data. It could well be that a good curve fit is obtained to data that improperly represent a good assay.

Suitably the quality control limits are common for both MGCC and pseudo data sets (IGCC). The method of the invention may be used to determine a range of analytes and is very suitable for the determination of an analyte in a liquid sample. It is particularly useful in immunodiagnostic tests for analytes such as free thyroxine, follicle stimulating hormone, thyroid stimulating hormone and cortisol. In the test kit of the invention there will generally be different template information for each batch of kits for any given test.

The method and test kit of the invention have advantages in random access testing that is now increasingly used. Random access testing allows a user to nominate any test(s) on any sample at any time. There is no necessity to retain samples until a reasonable batch size has been attained. Individual samples can be presented for testing as required. In order to control the cost of calibration, some form of reduced calibration is required for random access analyzers since the cost of establishing a full calibration curve every time a sample is presented would otherwise be prohibitive. The invention offers the considerable advantage of reduced calibration. It has the additional advantage that the calibration information can be stored and used over a period of time.

The invention is illustrated by the following Example:

EXAMPLE

A method was developed for two point calibration of immunoassays by using various parameters determined from two standards and calibration curves obtained earlier by means of multiple-point determination. The prerequisite for this method is a reproducible working procedure, i.e., as assured by the fully integrated "Amerlite" system. In experimental investigations immunoassays Free Thyroxine (FT4), Follicle Stimulating Hormone (FSH), Thyroid Stimulating Hormone (TSH) and Cortisol were determined in human serum pools over a period of weeks with both full calibration and two point calibration. Comparisons of the results thereby obtained showed that the means of the concentrations and the precision for the alternative calibration procedure differed negligibly, even if stressed reagents were used. With the two point recalibration procedure presented here one can considerably reduce the time and effort spent on calibration.

Procedure

The "Amerlite" reduced calibration system can be summarized as follows:

a) Preparation of Manufacturer Generated Standard Curves (MGCC), including test criteria for acceptability of the data.

b) two or three point calibration.

c) adjustment of the MGCC data, deriving "Pseudo" calibration points for subsequent curve-fitting.

d) Fitting of functional forms to the assay data MGCC or Pseudo calibrators, including test criteria for acceptability of both the numerical fit of the curve to the assay data, and of the shape characteristics of the assay data.

e) Reporting of sample concentrations interpolated from the fitted pseudo curve.

The step (a), the MGCC, is determined by Kodak Clinical Diagnostics Limited during the kit manufacturing process.

Steps (b–e) occur as a part of each assay run on the "Amerlite" system.

The system of reduced calibration involves the use a stored full calibration reference curve (MGCC).

The objective of the MGCC is to provide a set of "representative" assay calibrator signals and concentration data, which will be stored in the instrument. To achieve this, sufficient assays are performed from a new batch to assure that a representative average may be formed. This MGCC is more suitable as a representative of the analyte dose-response curve than a single assay.

Based on the concept of simple scaling for curve adjustment, a method of combination of a multiplicity of standard assays to form a pooled set of data has been developed. The individual sets of assay data are merged by scaling into a single set of data having a minimum coefficient of variation (% CV).

At each Reference Calibrator point, the pooling algorithm returns an estimate of the % CV of the pooled signal estimate, which enables comparison with the expected % CVs, and rejection of poor assays.

Delta checks (defined below) are made by Quality Control, for assurance that at each Reference Calibrator individual pooled signals fall within certain ratios of each other (uniquely defined for every analyte). It is the Delta ratios of the signals that determine the shape of the dose-response curve.

Quality control of the "Light Index" (defined as the signal level for the highest-signal Reference Calibrator concentration) is applied to each of the test assays.

Finally, a curve is fitted to the pooled signal estimates.

If the curve fit is satisfactory, then the MGCC is judged to have passed Quality Control and is suitable for release.

The results of the assay pooling (Reference Calibrator concentrations and pooled signal estimates), are transferred to the instrument to form the stored MGCC.

Fitting of curves to signal and concentration data is needed at several stages of the calibration procedure.

The shape of the dose-response curve is determined by the assay binding chemistry, the signal generation process e.g. enhanced-luminescence, temperature, reagent stress and other conditions, and also by the measurement errors.

The procedure uses a separately modified logistic curve fitting function for immunoassays and competition assays.

The form adopted for competitive assays has a four-parameter logistic function, to which is added a one-parameter modifier function. The magnitude of the added modifier component is carefully controlled to prevent gross departure from the underlying logistic shape.

For Immunometric assays a four-parameter logistic forms the underlying function, with a one-parameter modifier function applied which is dependent on the signal level. Again the magnitude of the modifier component is carefully controlled to prevent gross departure from the underlying logistic shape.

The non-linear least-squares fitting algorithm used in the curve fitting process uses classical minimization techniques (based on Taylor series-expansion in parameter adjustments of the sum of squares to be minimized), with iterative improvement of the parameter estimates. Parameter constraints are applied to ensure physically sensible values.

Interpolation and extrapolation routines are included in the curve fitting process that return both signal-from-concentration and concentration-from-signal values.

The acceptability of the curve fitted to the data is assessed by calculating the worst-case fractional deviation of any of the individual replicate data points from the fitted curve. This single figure includes both a component due to the spread in the data themselves, and a component due to the miss-fit of the curve. A pre-defined limit is applied to test for an acceptable fit.

During routine use of the instrument, the MGCC data is used to define the shape of the curve. Calibration was carried out using two calibrators in this example.

In this example the calibrators had the same concentration as the standards that were used when creating the MGCC data. However, this is not essential.

The method of re-calibration was based on a piece-wise linear re-scaling method which is outlined below:

1) A curve was fitted to the stored MGCC signal and concentration data.
2) At each Calibrator concentration a "Reference signal" was read from the curve. Scaling was applied to force the re-scaled Reference Signals to match the Calibrator signals.

The method re-scaled locally around each Calibrator signal, so that the re-calibrated MGCC curve exactly matched at two points.

For MGCC signals below the lowest Reference Signal, a simple proportional scaling was applied. This made the curve pass through the lowest Calibrator signal.

For MGCC signals between adjacent pairs of Reference Signals, piece-wise linear scaling was applied. This made the curve pass through the corresponding adjacent pairs of Calibrator signals.

For MGCC signals above the highest Reference Signal, a simple proportional scaling was applied. This made the curve pass through the highest Calibrator signal.

In the simplest case, the relationship of the actual measured Calibrator signals to the derived Reference Signal will be a simple linear proportionality. The slope of the relationship indicates a "scaling" change, which may be for example an actual change of signal amplification or a change in signal-generation reagent enhancement.

The algorithm forced the actual Calibrator signals and the derived Reference Signals to lie on the re-scaled curve.

The result of the re-scaling algorithm was a new set of data consisting of the MGCC stored concentration values and the pseudosignals.

3) A curve was then fitted to the pseudo rescaled signals using the modified logistic function. However, an alternative curve fitting routine could have been applied.
4) Interpolation using the fitted curve was used to obtain the concentration of patient or control samples.
5) The quality of the re-calibration was monitored in as outlined previously.

The working steps from the pipetting of samples and reagents, through the necessary incubation and washing steps, up to photometric measurement were carried out following the protocols outlined in "Amerlite" package inserts. The optimum sample volumes and the incubation times for the individual reaction steps are specified for every analyte measured in each package insert.

Heterogeneous immunoassays for FT4, FSH, TSH and Cortisol were used in the investigations. The procedures thus included competitive assays and Immunometric assays.

For a number of the investigations pooled human serum of differing analyte concentrations were made up, aliquots were then frozen and used for a number of experiments. All experiments included the measurement of control serum that covered the clinically important ranges of each assay.

In most investigations, the reagents were treated according to the recommendations in the product inserts. Due to the possible effect of reagent stress, e.g. storage at elevated temperatures, investigations also included reagents exposed to different storage conditions. The validity of the recalibration procedure was assessed via a comparison of data obtained on the one hand by full calibration and on the other with recalibration using two calibrators.

Concentration means and coefficient of variation values (% CV) were determined for a number of samples using both calibration procedures.

In summary, the process of the invention can be described as follows (see FIGS. 1–5):

Each analyzer is shipped with a manufacturer-generated calibration curve, or machine-generated Cal Curve "(MGCC)", FIG. 1, wherein for each of N selected concentration values $C_A$, $C_B$, $C_C$ . . . $C_F$, (N=6) there is stored in a look-up table (equivalent to plotting a curve) an average expected (or "reference") signal $R_A$, $R_B$ . . . $R_F$, e.g., measured in photons, as determined from many readings of each concentration (e.g., 20) on several analyzers (e.g., 3).

Figure 2:
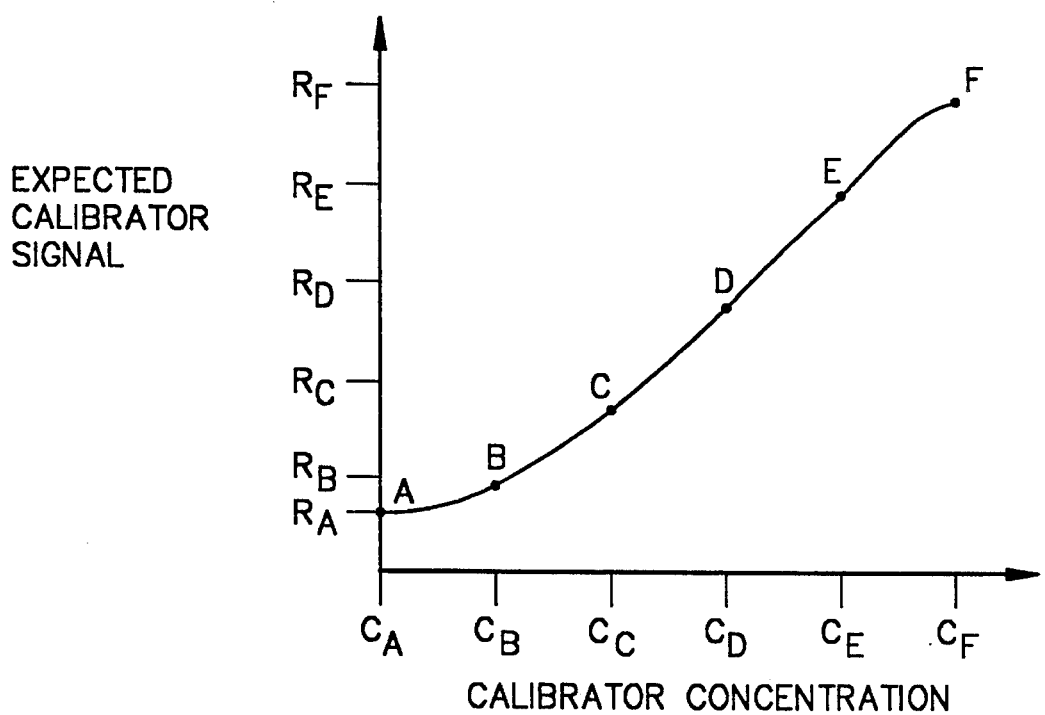
Figure 3:
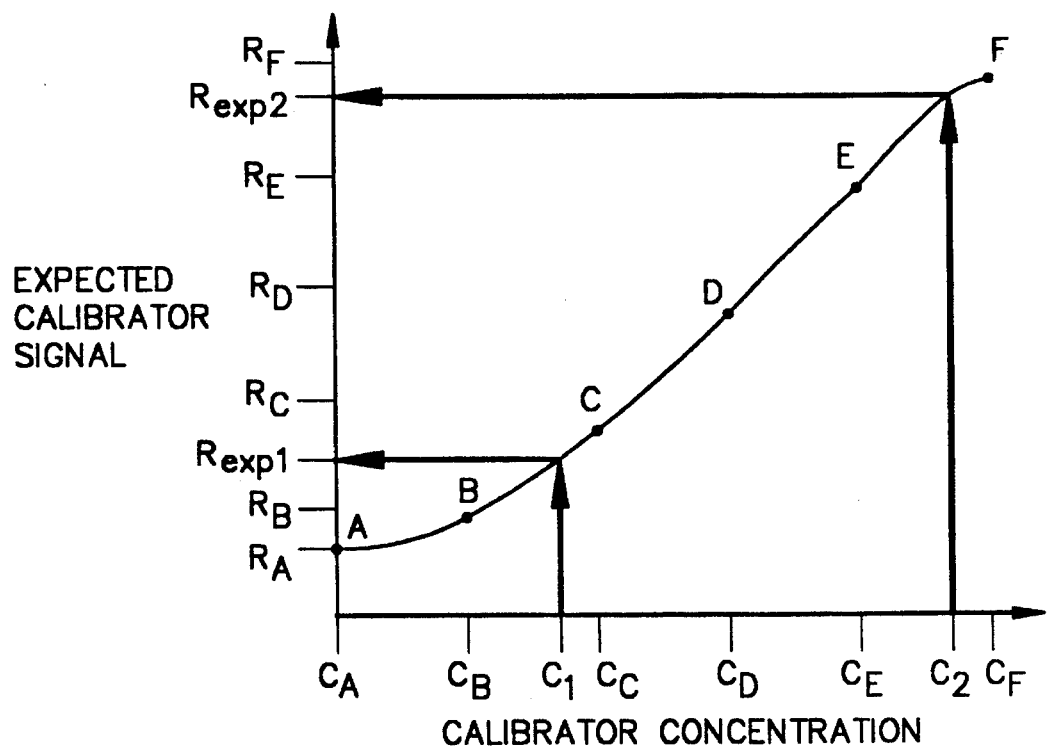

Then, each analyzer is programmed to, and will fit, a curve, FIG. 2, to these 6 data points so that any other concentration ($C_i$) can produce an expected signal value ($R_{expi}$).

However, the MGCC curve is likely to become outdated over time, at any given field analyzer. To correct for this, two calibrators $C_1$ and $C_2$ are tested at the field site. They are expected to produce a signal value of $R_{exp1}$ and $R_{exp2}$, FIG. 3. However, they instead produce some different actual value $R_{act1}$ and $R_{act2}$.

In accordance with the invention, the analyzer then takes the ratio of $R_{act1}/(R_{exp1})$ for $C_1$ and uses it as a multiplier against any of the $R_A$, $R_B$ . . . $R_F$ that is for a concentration $C_A$, $C_B$ . . . $C_F$ that is less than $C_1$, to achieve a pseudosignal PS. That is, the process is $PS_A = R_{act1}/R_{exp1} \cdot R_A$, $PS_B = R_{act1}/R_{exp1} \cdot R_B$. etc, for each of the six points corresponding to a concentration less than $C_1$. At the upper end, $C_2$, for all of the six data points of FIG. 1 that are higher than $C_2$ in concentration, the multiplier is $R_{act2}/R_{exp2}$ so that pseudosignal $PS_F$, for example, if that is for $C_F > C_2$, becomes $R_{act2}/R_{exp2} \cdot R_F$.

Then, any of the remainder data points for $C_C$, $C_D$ etc between $C_1$ and $C_2$, one simply solves for the equation: $PS_{remainder} = m \cdot (R_{expremainder} - R_{exp1}) + R_{act1}$; where $m = (R_{act2} - R_{act1})/(R_{exp2} - R_{exp1})$.

Figure 4:
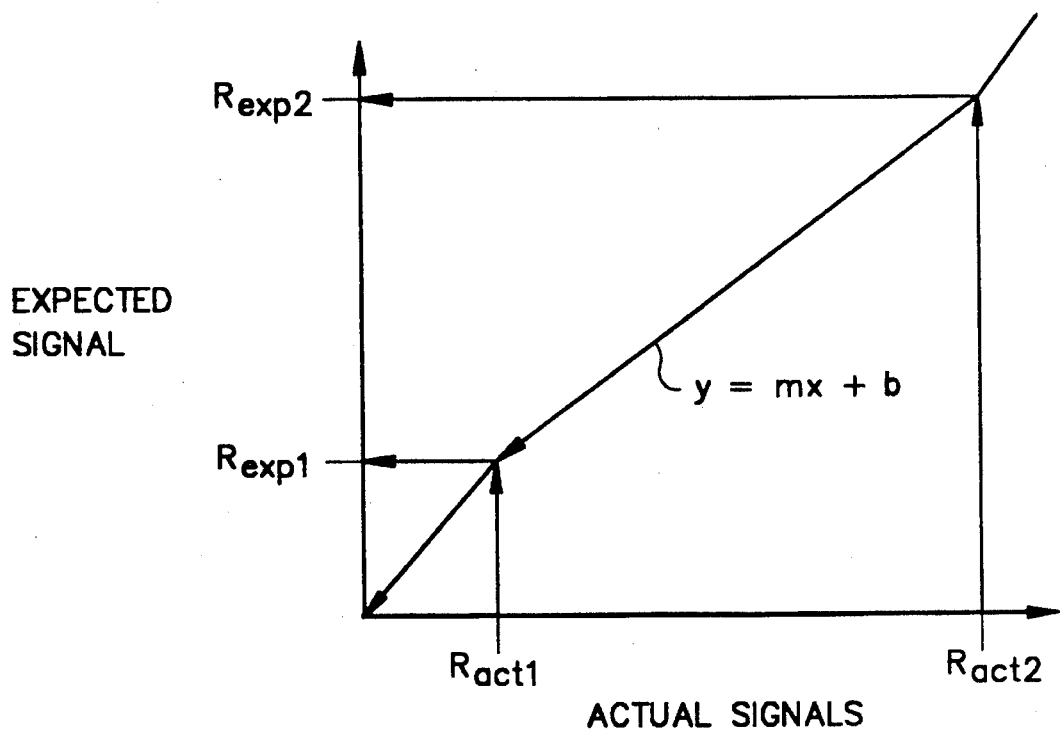

Graphically, the result is to create a relationship shown in FIG. 4, where the actual instrument signals $R_{act1}$ and $R_{act2}$ are plotted on the X-axis, and the expected signals $R_{exp1}$ and $R_{exp2}$ on the Y-axis. Then, the interpolation for the pseudosignals below $R_{act1}$, above $R_{act2}$, and in between, follows from the procedure noted above.

Figure 5:
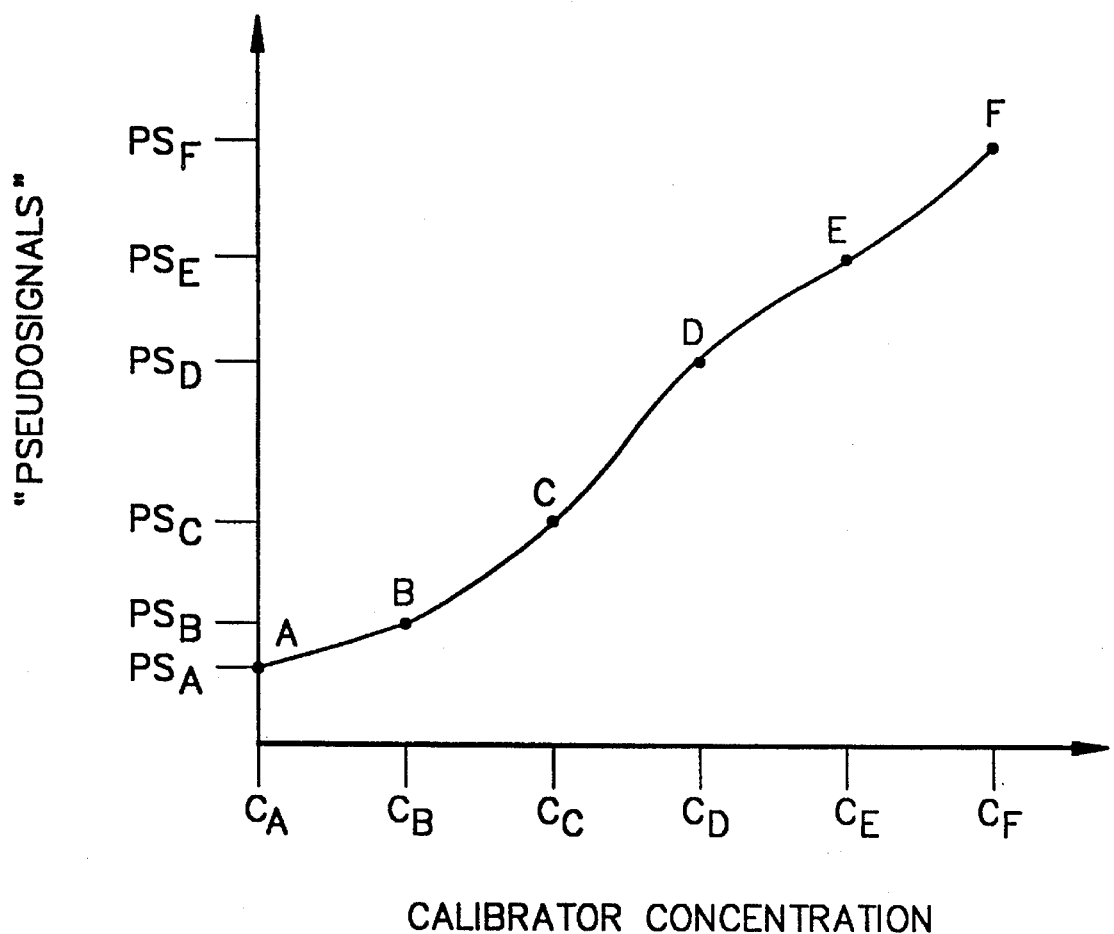
Figure 6:
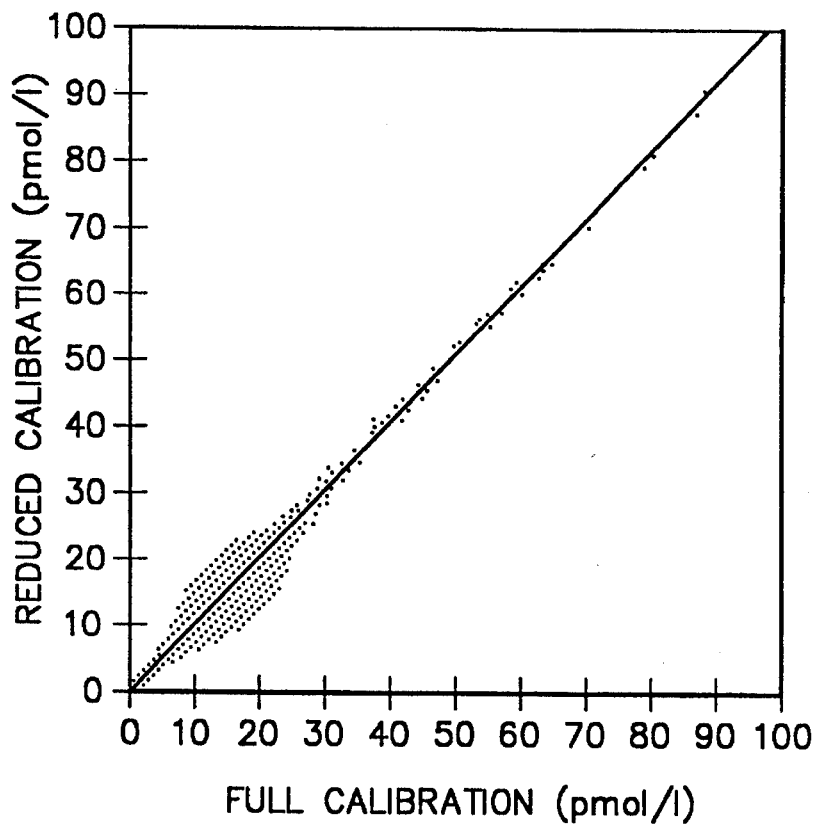
FIGS. 6–9 are plots of reality on the X-axis versus results obtained by the invention on the Y-axis, to depict performance, for four different analytes.
Figure 7:
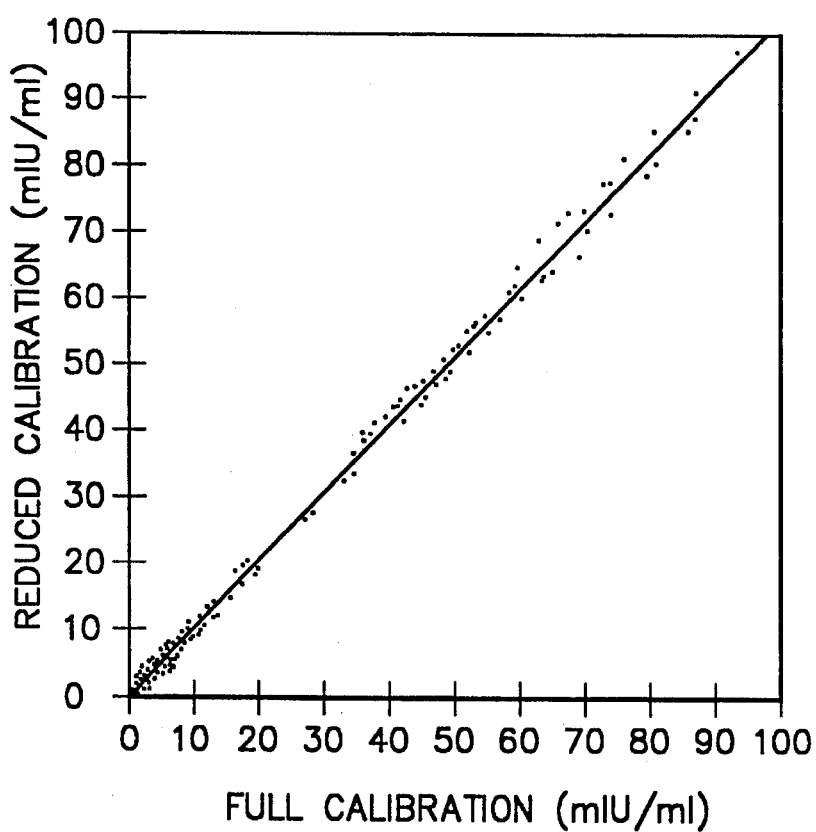
Figure 8:
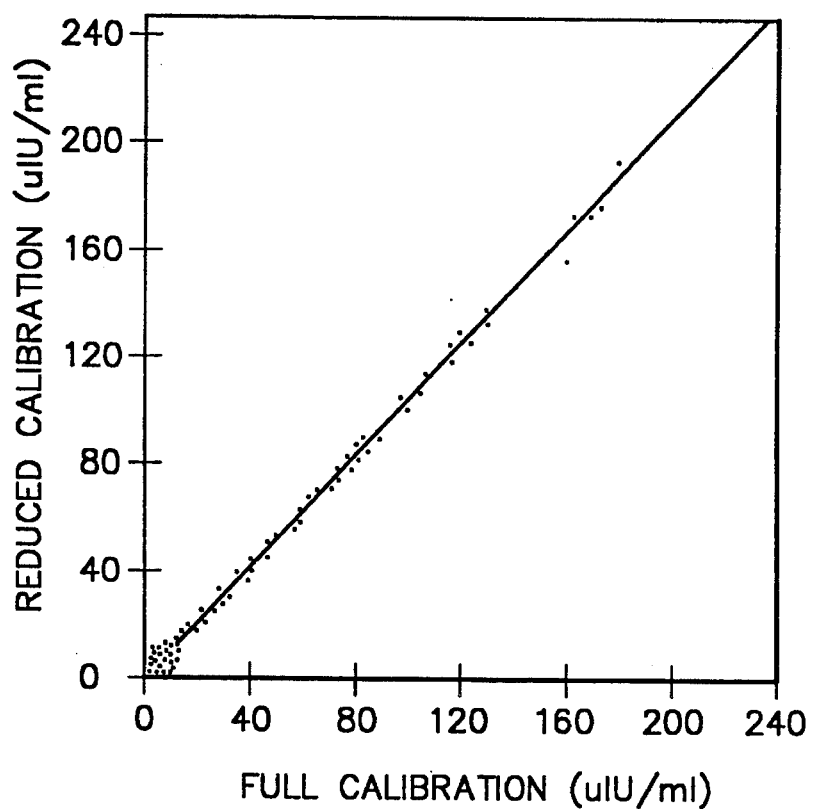
Figure 9:
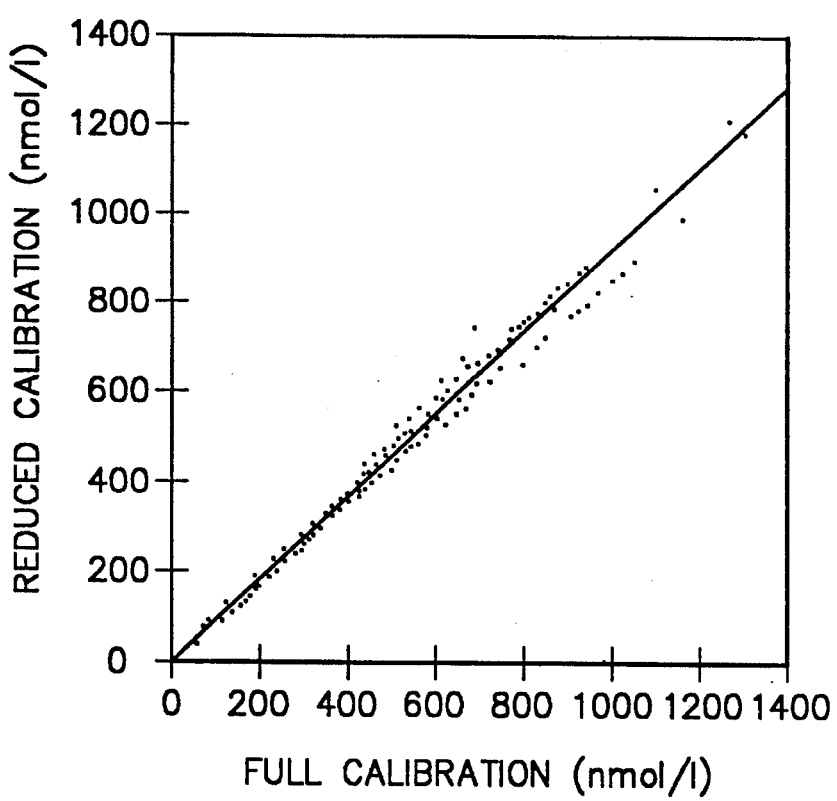

The new pseudosignals $PS_A$ . . . $PS_F$ for concentrations $C_A$ . . . $C_F$ are then ascertained, such as by plotting them versus the concentrations, of which FIG. 5 is a simplified example, to get the revised calibration data. The points between are obtained by the analyzer fitting a curve to these points of data (or a look-up table). It is the latter that is then used for all future testing on the analyzer, until such time as it is recalibrated with 2 new calibrators $C_Q$ and $C_R$, which may or may not equal $C_1$ and $C_2$, respectively, in value.

Any suitable computer programming can be used to carry out this invention in the analyzer. The attached Appendix shows an illustrative example in C code.

An actual working example follows. In this example, the signal output decreases with increasing concentration, which is the reverse of the example of FIGS. 1–5:

Materials

Amerlite FT4 assay coated wells (donkey anti-sheep, binds>0.2fmol(30 pg) sheep lg/well)

Amerlite FSH assay coated wells (sheep polyclonal anti-FSH)

Amerlite TSH Assay (monoclonal) coated wells (mouse monoclonal anti-Beta subunit of TSH)
Amerlite Cortisol assay coated wells (donkey anti-sheep)
Amerlite assay reagents
Amerlite standards
Conjugate reagents
Amerlite Signal generating reagent buffer
Amerlite Signal generating tablets A and B
Amerlite wash reagent buffer Results: Effect of two point calibration on assay performance Example of correction.
Amerlite FT4
Manufacturer Generated Calibration Curve data

| Calibrator | Calibrator concentration pmol/l | Light Signal |
|---|---|---|
| 1 | 0 | 12889.9 |
| 2 | 6.48 | 6899.58 |
| 3 | 13.30 | 4572.45 |
| 4 | 28.50 | 2384.63 |
| 5 | 62.10 | 849.51 |
| 6 | 101.9 | 221.37 |

Assay run after 38 days

| Calibrator | Calibrator concentration pmol/l | Light Signal | |
|---|---|---|---|
| 1 | 0 | 11337.70 | |
| 2 | 6.48 | 5800.77 | Calibrator 1 (y0) |
| 3 | 13.30 | 3792.44 | |
| 4 | 28.50 | 1882.07 | |
| 5 | 62.10 | 551.52 | Calibrator 2 (y1) |
| 6 | 101.9 | 92.10 | |

Rescaling of lower region of calibration curve

MGCC Calibrator concentration = 6.48 pmol/l
Signal = 6899.58 (u0)
Assay run after 38 days
Low calibrator concentration = 6.48 pmol/l
Signal = 5800.77 (y0)
Slope = y0/u0 = 0.8407
Scaling applied below first calibrator = Slope * MGCC light signal
Calibrator 1 pseudo signal = 10837.08
Rescaling applied above the top calibrator
MGCC Calibrator concentration = 62.10 pmol/l
Signal = 849.51 (u1)
Assay run after 38 days
High calibrator concentration = 62.10 pmol/l
Signal = 551.52 (y1)
Slope = y1/u1 = 0.6492
Scaling applied above top calibrator = Slope * MGCC light signal
Calibrator 6 pseudo signal = 66.16
Rescaling the intermediate segment between calibrators
Slope = (y1-y0) / (u1-u0) =
(551.52-5800.77)/(845.91-6899.58) =
(−5249.25)/(−6053.67) = 0.867
Scaling applied between calibrators =
(slope * (MGCC signal - u0)) + y0
Calibrator 3 pseudo signal =
0.8671 * (4572.45 - 6899.58) + 5800.77 = 3782.92
Calibrator 4 pseudo signal =
0.8674 * (2384.63 - 6899.58) + 5800.77 = 2318.20

| Calibrator | Full Calibration Light Signal | Reduced Calibration curve (pseudo points) |
|---|---|---|
| 1 | 11337.70 | 10837.08 |
| 2 | 5800.77 | 5800.77 |
| 3 | 3792.44 | 3782.92 |
| 4 | 1882.07 | 2318.20 |
| 5 | 551.52 | 551.52 |
| 6 | 92.10 | 66.16 |

| Controls | Full Calibration concentration pmol/l | Reduced Calibration Concentration pmol/l |
|---|---|---|
| 1 | 4.58 | 4.57 |
| 2 | 15.28 | 16.22 |
| 3 | 44.57 | 46.67 |

This section presents a selection of reduced calibration assay performance results.

Using selected calibrator combinations results are outlined for assay precision and correlation between full and reduced calibration procedures.

Inter-Assay Precision

The effect of the two point calibration algorithm on the run to run precision for each analyte was examined. For each analyte approximately ten assays were performed with both full and two point calibration. These assays consisted of a standard curve and controls.

Results for each of the analytes are shown in Tables 1–4.

TABLE 1

FT4 (pmol/l)

| | Full Calibration | | | Reduced Calibration | | |
|---|---|---|---|---|---|---|
| Controls | 1 | 2 | 3 | 1 | 2 | 3 |
| Mean | 5.18 | 19.26 | 35.26 | 4.68 | 18.75 | 34.58 |
| Standard Deviation (SD) | 0.29 | 0.91 | 1.98 | 0.36 | 0.73 | 1.38 |
| % CV | 5.6 | 4.7 | 5.6 | 7.7 | 3.8 | 4.0 |

TABLE 2

FSH (mIU/ml)

| | Full Calibration | | | | Reduced Calibration | | | |
|---|---|---|---|---|---|---|---|---|
| Controls | 1 | 2 | 3 | 4 | 1 | 2 | 3 | 4 |
| Mean | 4.65 | 10.82 | 24.7 | 61.8 | 4.67 | 10.88 | 24.8 | 61.2 |
| SD | 0.33 | 0.74 | 1.24 | 3.38 | 0.34 | 0.88 | 1.25 | 3.21 |
| % CV | 7.1 | 6.8 | 5.0 | 5.5 | 7.3 | 8.1 | 5.0 | 5.2 |

TABLE 3

TSH (uIU/ml)

| | Full Calibration | | | | Reduced Calibration | | | |
|---|---|---|---|---|---|---|---|---|
| Controls | 1 | 2 | 3 | 4 | 1 | 2 | 3 | 4 |
| Mean | 0.17 | 6.55 | 27.65 | 0.18 | 0.16 | 6.61 | 27.77 | 0.17 |
| SD | 0.014 | 0.343 | 1.139 | 0.021 | 0.02 | 0.3 | 1.074 | 0.025 |
| % CV | 8.2 | 5.2 | 4.1 | 11.7 | 12.5 | 4.5 | 3.9 | 14.7 |

TABLE 4

| | Cortisol (nmol/l) | | | | | | | |
|---|---|---|---|---|---|---|---|---|
| | Full Calibration | | | | Reduced Calibration | | | |
| Controls | 1 | 2 | 3 | 4 | 1 | 2 | 3 | 4 |
| Mean | 41.0 | 275 | 688 | 780 | 39.6 | 277 | 684 | 775 |
| SD | 5.46 | 21.67 | 45.11 | 51.70 | 6.24 | 22.78 | 50.82 | 74.05 |
| % CV | 13.3 | 17.9 | 6.6 | 6.6 | 15.8 | 8.2 | 7.4 | 9.6 |

The above example illustrates the general principle of the Reduced Calibration procedure for a competitive assay.

This following section presents a selection of reduced calibration assay performance results.

Using selected calibrator combinations results are outlined for assay precision and correlation between full and reduced calibration procedures.

Inter-Assay Precision

The effect of the two point calibration algorithm on the run to run precision for each analyte was examined. For each analyte approximately ten assays were performed with both full and two point calibration. These assays consisted of a standard curve and controls.

Results for each of the analytes are shown in Table 5.

TABLE 5

| Analyte | FT4 (pmol/l) | FSH (mIU/ml) | TSH (uIU/ml) | Cortisol (nmol/l) |
|---|---|---|---|---|
| Correlation Coefficient | 0.9978 | 0.9993 | 0.9996 | 0.9951 |
| Slope of Line | 1.012 | 1.014 | 1.033 | 0.9284 |
| Intercept | −0.1479 | −0.08977 | −0.151 | 10.76 |
| Degrees of freedom | 973 | 322 | 498 | 228 |

Patient Correlation

Patient samples were analyzed using Full and reduced Calibration. The correlation results are shown in Table 5. FIGS. 6–9 the scatter of the two point calibration versus full calibration.

The results are illustrated by FIGS. 6–9 of the accompanying drawings which are calibration correlation plots for FT4 (FIG. 6), FSH (FIG. 7), TSH (FIG. 8) and cortisol (FIG. 9) respectively.

The two point recalibration procedure developed re-scales locally around each Calibrator signal, so that the re-calibrated template curve exactly matches at two points.

The Reduced Calibration procedure outlined compensates for changes in curve shape. The performance of Competitive and Immunometric (sandwich type) assays were similar for reduced calibration.

A comparison of concentration means and CVs yielded good agreement for two point calibration procedures for FT4, FSH, TSH and Cortisol.

Experiments on stressed reagents showed that the two point calibration procedure was also capable of correctly calculating curves that were not identical with the reference curve. This is particularly important when the same prepared reagent is to be used for several runs.

Two point recalibration involving the split scaling of the calibration curves in the lower, middle and upper regions described above thus provides a good method for clearly reducing the calibration requirements for immunoassay tests without reducing the necessary precision and accuracy of the results.

APPENDIX
REPRESENTATIVE PROGRAM FOR SUBROUTINE
TO RECALIBRATE THE MGCC RELATIONSHIP
© Kodak Clinical Diagnostics Limited 1993
All Rights Reserved

```
*FH
*FHFN    Function Name: scale_mgs_data
*FH
*FH      Purpose:
*FH
*FH      Performs the piecewise-linear-rescaling of Manufacturer
*FH      Generated Standard data to the derived Calibrator signal
*FH      reference data. Places the result in the vector pseudo[ ]
*FH      for subsequent curve-fitting.
*FH
*FH      RESTRICTIONS:
*FH
*FH      The re-calibration method is expected to use no more than two
*FH      or three Calibrators; however this routine has been written
*FH      to handle any number of Calibrators. Note that the number of
*FH      Calibrators 'ncal' *MUST* always be less than the number of
*FH      MGCC Standards 'nstds'.
*FH
*FH      Operation:
*FH
*FH      Uses piecewise-linear transformation of the MGCC signal data
```

APPENDIX
REPRESENTATIVE PROGRAM FOR SUBROUTINE
TO RECALIBRATE THE MGCC RELATIONSHIP
© Kodak Clinical Diagnostics Limited 1993
All Rights Reserved

```
*FH    to match the measured re-Calibration signals to the expected
*FH    Calibrator signals, and then creates the 'pseudo Standard'
*FH    signals ready for a subsequent smoothing curve fit.
*FH
*FH    Note that the re-Calibrator concentrations do not need to be
*FH    identical to any of the MGCC concentrations, although they
*FH    should lie within the span of the MGCC concentrations.
*FH
*FH    Inputs:
*FH
*FH       ENTRY_DATA.nstds         ;number of MGCC Standard points
*FH       .conc[ ]                 ;concentrations of the MGCC Standard
*FH                                 Points
*FH
*FH       MGSC_DATA.ncal           ;number of re-Calibrator points
*FH       .cal_cnc[ ]              ;concentrations of the re-Calibrator
*FH                                 points
*FH       .cal_ref[ ]              ;expected signals, re-Calibrator points
*FH       .cal_sig[ ]              ;measured signals, re-Calibrator points
*FH       .mgs_sig[ ]              ;supplied signals, MGCC Standard points
*FH
*FH    Outputs:
*FH
*FH       ENTRY_DATA.pseudo[ ]     ;the 'pseudo' Standard signals vector
*FH       (return)                 ;the segment slope mis-match 'shape factor'
*FH
*FH    Effects:
*FH
*FH
*FH
*FH
*FH
*FH***********************************************************************
*/
float scale_mgs_data(ENTRY_DATA *input, MGSC_DATA *risc)
{
        float slope,smax,smin,u0,u1,y0,y1;
        int cal,std;
        /*-------------------------
        re-scale the initial portion
        -------------------------*/
        u0 = risc->cal_ref[0];      /*Expected reference signal */
        y0 = risk->cal_sig[0];      /*Measured Calibrator signal */
        slope = y0 / u0             /*Chord slope in first segment*/
        smax = slope;               /*Maximum slope */
        smin = slope;               /*Minimum slope */
        /*--------------------------------------------------------
        handle a single re-Calibrator case;
        simple proportional re-scaling of all the MGSC data
        --------------------------------------------------*/
        if (risc->ncal <= 1)
        {
        for (std = 0; std < input->nstds; std++)
        input->pseudo[std] = slope * risc->mgs_sig[std];
        return (ZERO);
{
/*-------------------------------------------
handle the general multiple re-Calibrators case;
re-scale MGSC data below the lowest calibrator
---------------------------------------------*/
for (std = 0; input->conc[std] < risc->cal_cnc[0]; std++)
input->pseudo[std] = slope * risc->mgs_sig[std];
/*---------------------------------------------------------------
re-scale the intermediate segments between Calibrators
---------------------------------------------------------------*/
for (cal = 1; cal < risc->ncal; cal ++)
    {
    u1 = risc->cal_ref[cal];
    y1 = risc->cal_sig[cal];
    slope = (y1-y0) / (u1-u0);
    smax = max(smax,slope);
    smin = min(smin,slope);
    for (; input->conc[std] < risc->cal_cnc[cal]; std++)
    input->pseudo[std] = slope * (risc->mgs_sig[std] - u0) + y0;
```

APPENDIX
REPRESENTATIVE PROGRAM FOR SUBROUTINE
TO RECALIBRATE THE MGCC RELATIONSHIP
© Kodak Clinical Diagnostics Limited 1993
All Rights Reserved

```
    u0 = u1;
    y0 = y1;
}
/*----------------------------------------------
re-scale the final segment above the top Calibrator
----------------------------------------------*/
slope = y1 / u1;
smax = max(smax,slope);
smin = min(smin,slope);
for (; std < input->nstds; std++)
input->pseudo[std] = slope * risc->mgs_sig[std];
/*----------------------------------------------
return the "shape factor", a constructed measure of the greatest
mismatch from true linearity between the piecewise-linear segments.
----------------------------------------------*/
return ((smax−smin) / (smax+smin));
}
```

What is claimed is:

1. A method of recalibrating in an analyzer, a calibration relationship between concentrations of analyte and analyzer-generated signals corresponding to those concentrations, using a factory-prepared relationship for N number of concentrations, wherein each concentration has an expected signal value $R_{exp}$, the method comprising the steps of:

a) selecting at least two calibrators of differing concentrations one being higher in analyte value than the other, so that one ($C_1$) is at a high concentration and one ($C_2$) at a low concentration, respectively, that are optionally independent of the value of the concentrations of said N number;

b) ascertaining actual signals $R_{act1}+R_{act2}$ produced by each of said at least two calibrators in said analyzer;

c) ascertaining which of said N number of concentrations $(C_i)_{low}$ have an expected signal value below the actual signal of said low concentration-selected calibrator of step a) and which concentrations $(C_i)_{high}$ have an expected signal value greater than the actual signal of said high concentration-selected calibrator of step a);

d) forming the ratio of $R_{act1}/R_{exp1}$ and $R_{act2}/R_{exp2}$, where $R_{exp1}$ and $R_{exp2}$ are predicted signals expected for concentration $C_1$ and $C_2$ using said factory-prepared relationship;

e) producing a corrected signal for each of said concentrations $(C_i)_{low}$ by multiplying each signal $(R_{exp})_{low}$ for each of said below concentration values by the ratio $R_{act1}/R_{exp1}$ and a corrected signal for each of said concentrations $(C_i)_{high}$ by multiplying each signal $(R_{exp})_{high}$ for each of said greater concentration values by the ratio $R_{act2}/R_{exp2}$;

f) for each of said N number of concentrations having values between $C_1$ and $C_2$, producing a corrected signal $PS_{remainder}$ in accord with the following formula:

$$PS_{remainder}=(R_{act2}-R_{act1})/(R_{exp2}-R_{exp1})\cdot(R_{expremainder}-R_{exp1})+R_{act1};$$

g) ascertaining the relationship for the corrected signals so obtained in steps e)–f) versus the N number of concentrations; and h) providing a best curve fit for data points between the N number of concentrations to obtain the recalibrated relationship.

2. A method as defined in claim 1, wherein N=6.

3. A method as defined in claim 1, wherein said signals are produced by an immunoassay.

4. A method as defined in claim 3, wherein said signals are produced in a liquid in a well.

* * * * *